(12) United States Patent
Dawson et al.

(10) Patent No.: US 10,183,095 B2
(45) Date of Patent: Jan. 22, 2019

(54) TREATMENT OF SKELETAL VOIDS WITH IMPLANTABLE SUBSTRATE HYDRATED WITH BONE MARROW CONCENTRATE

(71) Applicant: SpineSmith Partners, L.P., Austin, TX (US)

(72) Inventors: Eileen Dawson, Austin, TX (US);
Kevin Dunworth, Austin, TX (US);
Theodore Sand, Austin, TX (US);
Matthew Murphy, Austin, TX (US);
John B. Rossman, Austin, TX (US);
Melissa Samano, Austin, TX (US);
Richard Suzuki, Austin, TX (US);
Katy Moncivais, Austin, TX (US)

(73) Assignee: SpineSmith Partners, L.P., Austin, TX (US)

( * ) Notice: Subject to any disclaimer, the term of this patent is extended or adjusted under 35 U.S.C. 154(b) by 0 days.

(21) Appl. No.: 14/921,826

(22) Filed: Oct. 23, 2015

(65) Prior Publication Data

US 2016/0114078 A1    Apr. 28, 2016

Related U.S. Application Data

(60) Provisional application No. 62/067,815, filed on Oct. 23, 2014.

(51) Int. Cl.

| | |
|---|---|
| *A61L 27/38* | (2006.01) |
| *A61L 27/56* | (2006.01) |
| *A61L 27/12* | (2006.01) |
| *A61L 27/20* | (2006.01) |
| *A61L 27/22* | (2006.01) |
| *A61L 27/24* | (2006.01) |

(52) U.S. Cl.
CPC ............ *A61L 27/12* (2013.01); *A61L 27/20* (2013.01); *A61L 27/22* (2013.01); *A61L 27/222* (2013.01); *A61L 27/225* (2013.01); *A61L 27/227* (2013.01); *A61L 27/24* (2013.01); *A61L 27/3834* (2013.01); *A61L 27/3847* (2013.01); *A61L 27/56* (2013.01); *A61L 2430/02* (2013.01)

(58) Field of Classification Search
CPC ...... A61L 27/12; A61L 27/56; A61L 27/3847; A61L 27/38; A61L 27/3821; A61L 27/3834; A61L 27/222; A61L 27/20; A61L 27/047; A61L 27/025
See application file for complete search history.

(56) References Cited

U.S. PATENT DOCUMENTS

| | | | | |
|---|---|---|---|---|
| 9,114,190 B2 * | 8/2015 | Flood | ........... | A61K 35/18 |
| 2002/0161449 A1 * | 10/2002 | Muschler | ........... | A61F 2/4644 |
| | | | | 623/23.51 |
| 2015/0010607 A1 * | 1/2015 | Francis | ........... | A61K 35/28 |
| | | | | 424/422 |

OTHER PUBLICATIONS

Baylink et al, Journal of Bone and Mineral Research, 1993, vol. 8, Suppl 2, pp. S565-S572.*
Chen et al. (2010) "Mechanobiology of Bone Development and Computational Simulations". In F. Bronner et al. (eds), Bone and Development, Topics in Bone Biology (p. 280, 282). London: Springer-Verlag.*
Bidarra et al "Injectable alginate hydrogels for cell delivery in tissue engineering" Acta Biomaterialia, 2014 (epub Dec. 12, 2013), vol. 10, pp. 1646-1662. (Year: 2014).*
Salgado et al "Bone Tissue Engineering: State of the Art and Future Trends" Macromolecular Bioscience, 2004, vol. 4, pp. 743-765. (Year: 2004).*

* cited by examiner

*Primary Examiner* — Allison M Fox
(74) *Attorney, Agent, or Firm* — Winstead PC

(57) ABSTRACT

The invention is directed to a bone void filler comprising a scaffold or matrix. The scaffold or matrix may include a porous inorganic matrix component. The bone void filler may include a cellular component containing cells, some of which are capable of making extracellular matrix resembling native bone tissue. The bone void filler may include an organic matrix, such as, an organic biopolymer that aids in cell retention and renders the scaffold or matrix moldable. The bone void filler may include growth factors and/or cytokines. The bone void filler may include a clotting agent.

15 Claims, 4 Drawing Sheets

TREATMENT OF SKELETAL VOIDS WITH IMPLANTABLE SUBSTRATE HYDRATED WITH BONE MARROW CONCENTRATE

CROSS-REFERENCES TO RELATED APPLICATIONS

This application claims the benefit under 35 U.S.C. § 119(e) of U.S. Provisional Patent Application No. 62/067,815 filed Oct. 23, 2014, which is incorporated herein by reference in its entirety as if fully set forth herein.

BACKGROUND OF THE INVENTION

The claimed invention relates generally to medical devices and procedures and more particularly to devices and methods for treating defects in the tissue of a living being.

To better treat our aging population, physicians are looking for new and better products and methods to enhance the body's own mechanism to produce rapid healing of musculoskeletal injuries and degenerative diseases. Treatment of these defects has traditionally relied upon the natural ability of these types of tissue to repair themselves. In many instances the body is unable to repair such defects in a reasonable time, if at all. Advances in biomaterials has allowed for the creation of devices to facilitate wound healing in both bone and soft tissues defects and injuries. Such devices are used in tissue regeneration as tissue (e.g. bone) graft scaffolds, for use in trauma and spinal applications, and for the delivery of drugs and growth factors.

Bone and soft tissue repair is necessary to treat a variety of medical (e.g., orthopedic) conditions. For example, when hard tissue, such as bone, is damaged as a result of disease or injury, it is often necessary to provide an implant or graft to augment the damaged bone during the healing process to prevent further damage and stimulate repair. Such implants may take many forms (e.g. plugs, putties, rods, dowels, wedges, screws, plates, etc.) which are placed into the tissue. Typically, such implants can be rigid, flexible, deformable, or flowable and can be prepared in a variety of shapes and sizes. For rigid implants (e.g. bone screws), the defect site is typically preconditioned by forming a depression, channel, or other feature (e.g. pre-tapped hole) therein in preparation for the application of the implant. For non-rigid structural repair materials (e.g. putties and pastes) to be conveniently used, they must be capable of being formed into a variety of complex shapes to fit the contours of the repair site. An accurately configured implant that substantially fills the defect site will enhance the integration of natural bone and tissue to provide better healing over time. For example, when repairing defects in bone, intimate load carrying contact often is desired between the natural bone and the bone substitute material to promote bone remodeling and regeneration leading to incorporation of the graft by host bone.

Current bone graft materials include autografts (the use of bone from the patient), allografts (the use of cadaver bone), and a variety of other artificial or synthetic bone substitute materials. Autografts are typically comprised of cancellous bone and/or cortical bone. Cancellous bone grafts essentially provide minimal structural integrity. Bone strength increases as the implant incorporates surrounding cells and new bone is deposited. For cortical bone, the graft initially provides some structural strength. However, as the graft is incorporated by the host bone, nonviable bone is removed by resorption significantly reducing the strength of the graft. The use of autograft bone may result in severe patient pain and other complications at the harvest site, and there are limitations to the amount of autograft bone that can be harvested from the patient. Allografts are similar to autografts in that they are comprised of cancellous and/or cortical bone with greater quantities and sizes being typically available. Disadvantages of allografts include limited supplies of materials and the potential for transmission of disease. The disadvantages of the existing products creates a need for a better devices and methods for treating defects in the tissue of a living being.

After blood, bone is the most commonly transplanted tissue and autografts/allografts are used in approximately 2.2 million orthopaedic procedures annually. However, the usage of autograft and allograft materials as bone substitutes carries a number of possible complications. In autografts, considered the gold standard in bone substitutes, bone graft material is limited to patient sample availability, and thus is not a suitable candidate material for larger bone defects. For example, an iliac crest bone graft involves a surgical procedure to recover bone and marrow from the patient's iliac crest. Such procedures are associated with chronic pain at the site of graft harvest and a limited volume of autograft, since the iliac crest usually doesn't completely regenerate after harvesting. The issues of donor site morbidity have been reported. Allograft, although more widely available and without the same complications associated with sample harvesting, can result in other complications to the patient, notably disease transmission. Over 96% of FDA recalled allograft tissues were musculoskeletal allografts as a result of contamination, improper donor evaluation, and recipient infections. Additionally, allograft materials have been shown to lack the osteoinductive capacities of autograft samples. Therefore, there exists a need for the development of a synthetic alternative for bone grafts. When considering choices for this type of tissue replacement, a number of key material parameters need to be evaluated. The material would need to be non-toxic, non-immunogenic, capable of bonding with the host bone, capable of supporting in-growth of new bone into the graft, and biodegradable. The graft itself would need also to have adequate surface area contact between the graft and recipient site. While this could be accomplished by modifying the graft site with a reamer, burr or bone shaver, use of these instruments can cause heat generation, which may result in tissue necrosis. An ideal device and process would be one in which the substrate closely mimics natural bone tissue and is deployed in such a manner as to take into consideration the biology of tissue remodeling at the site of injury.

Wound healing in response to injury involves the coordination of a large number of complex cellular and molecular events within the body. This response is defined by the need for cells to respond to signals from the pathologic site, mobilize and migrate to the site of injury, secrete trophic factors, possibly proliferate, promote formation of blood vessels, and, eventually, promote synthesis of extracellular matrix to restore the structure and function of the damaged tissue. These cellular processes are driven by a wide variety of proteins, growth factors, and cytokines that act to control cellular functions. The contribution of cells is often overlooked in biomaterials-based approaches for orthopedic healing, but ultimately cells present at the treatment site, whether transplanted or recruited endogenously, that are responsible for new tissue generation and remodeling. It has recently been reported that many FDA-cleared biomaterials for bone healing are not efficient at retaining cells and, in many instances, were cytotoxic and had pH values less than 7 or greater than 10 when reconstituted. Materials that were not easily soluble (allograft bone and calcium phosphates) were most successful at retaining bone marrow MSCs and inducing osteogenic gene expression in an in vitro simulation of surgical graft preparation.

In addition to the effects of materials on cells, the source and number of cells must be considered. Many in vivo studies combine biomaterials with culture-expanded autologous or allogeneic cells as an implantable graft. Although this is convenient to standardize "doses" of therapeutic agents and seemingly control one variable of the regenerative paradigm, the clinical translation of this lab-oriented approach raises potential regulatory issues with the Food and Drug Administration (FDA) and other agencies. The usage of autologous cells at the point-of-care is an appealing alternative with fewer regulatory requirements and a decreased risk of cell contamination or rejection. A growing amount of data has suggested differences in clinical outcomes in non-union fracture, rotator cuff tear, avascular necrosis, and other orthopedic injuries based on the concentration of MSCs present in bone marrow. The influence of concentration of non-cultured, freshly obtained MSCs on bone formation when combined with HA granular particles is unknown.

Autologous bone grafts are successful because they are comprised of a number of components necessary for tissue regeneration: progenitor cells from the bone marrow, an extracellular matrix to support cellular growth, and osteogenic proteins and growth factors. In order to successfully create new tissue, all three factors need to be integrated, combining both autologous and synthetic materials in order to create an implantable device that elicits normal tissue restoration and achieves full repair.

SUMMARY OF THE INVENTION

Critically-sized bony defects arise from traumatic injury, tumor resection, autologous bone graft harvesting, and surgical procedures including spinal fusion. Autografts, considered the gold standard in bone substitutes, are impractical for use in larger defects as graft size would be limited to patient sample availability. Additionally, pain as well as local donor site morbidity are commonly reported at the site of graft harvesting. Autografts are successful in defect treatment because they combine a number of key aspects necessary for tissue growth. Successful bone regeneration requires contributions from all aspects of the "tissue engineering paradigm": cells, scaffolds, and biochemical/biomechanical signals.

Significant research has investigated various biomaterials and scaffolding techniques with osteoconductive or osteoinductive properties. Among these biomaterials is hydroxyapatite (HA), the primary form of calcium phosphate comprising the inorganic portion of bone, which has consistently demonstrated an ability to promote bone growth in vivo. Most commonly, monolithic scaffolds are utilized, usually conforming to the pre-determined shape of defects created in animal models. In clinical application, this type of scaffold would be impractical. An implanted scaffold would need to fill the entire volume of the defect, but having a pre-formed scaffold would limit its application to defects of specific sizes or require the physician to modify the graft or the graft site. This modification could have deleterious effects to the patient in that use of a reamer or burr to change the defect site can cause heat generation potentially resulting in local tissue necrosis. Ultimately, a moldable formulation may reduce surgical time as well as avoid additional bone loss or trauma to the surrounding tissue area. It would therefore be advantageous for the scaffolding material to be moldable to irregular geometries present in most clinical cases in order to completely fill the defect and bridge the native bone.

There are, however, a number of physical characteristics of bone that would need to be retained. The inclusion of porosity in the HA scaffolds cannot be understated, as there is typically a correlation between the extent and interconnectivity of pores and the scaffold's ability to regenerate bone. This characteristic can be achieved with ceramics by employing a granular or microparticle formulation. This approach has been validated in limited studies without specific tailoring of granule porosity or surface area nor thorough characterization of the cellular component of the graft.

An embodiment of the invention is directed to a filler for repair or regeneration of bone tissue. The filler incorporates the use of a scaffold matrix that comprises a porous granule, a cellular component, and an organic biopolymer. Other embodiments may include a growth factor and/or cytokine component.

An embodiment of the invention includes using a growth factor comprising at least one of vascular endothelial growth factor and plate-derived growth factor. In other embodiments, a cytokine is also added to the filler.

An embodiment of the invention includes using a growth factor comprising an autologous growth factor that has been concentrated from a biological fluid. In some embodiments, the concentrated biological fluid comprises at least one of a platelet poor fraction of blood and bone marrow.

An embodiment of the invention includes a porous granule that has a porosity between about 50% and about 95% by volume. In another embodiment, the porous granule comprises a porosity between about 3% and about 15% by volume.

An embodiment of the invention uses a porous granule that is formed from a composition selected from the group consisting of calcium phosphate, mono calcium phosphate, tricalcium phosphate, tetra calcium phosphate, octacalcium phosphate, hydroxyapatite, carbonate apatite, fluoro apatite. In another embodiment, the porous granule also comprises one or more of silicon, strontium, or magnesium.

An embodiment of the invention uses an organic biopolymer comprising one or more of collagen, gelatin, fibrinogen, vitronectin, fibronectin, albumin, peptides, chitin, alginate, cellulose, carboxymethycellulose. In other embodiments, the organic biopolymer may comprise a gelatin.

An embodiment of the invention uses a cellular component comprising autologous bone marrow. In some embodiments, the autologous bone marrow is filtered to remove at least one of red blood cells and extracellular components. An embodiment of the invention uses a cellular component comprising autologous adipose tissue. In some embodiments, the autologous adipose tissue comprises progenitor cells. An embodiment of the invention uses a cellular component comprising concentrated autologous progenitor cells. In some embodiments, the cellular component comprises concentrated allogeneic progenitor cells.

An embodiment of the invention includes the use of a clotting agent.

An embodiment of the invention is directed to a method that incorporates the use of concentrated autologous cells, including progenitor cells, which are known to support the body's natural response to injury and promote bone healing, delivered directly to the site of injury while seeded on a biomimetic substrate. In this way, the highest concentration of progenitor cells is delivered to the site of injury in combination with an osteogenic implant in the smallest volume possible, minimizing the implantation space while maximizing the regenerative capabilities of the implant. This method will be applicable for any defect within the body. This will include defects within the skeletal system including spine, pelvis, and extremities.

DETAILED DESCRIPTION OF EXEMPLARY EMBODIMENTS

Figure 1:
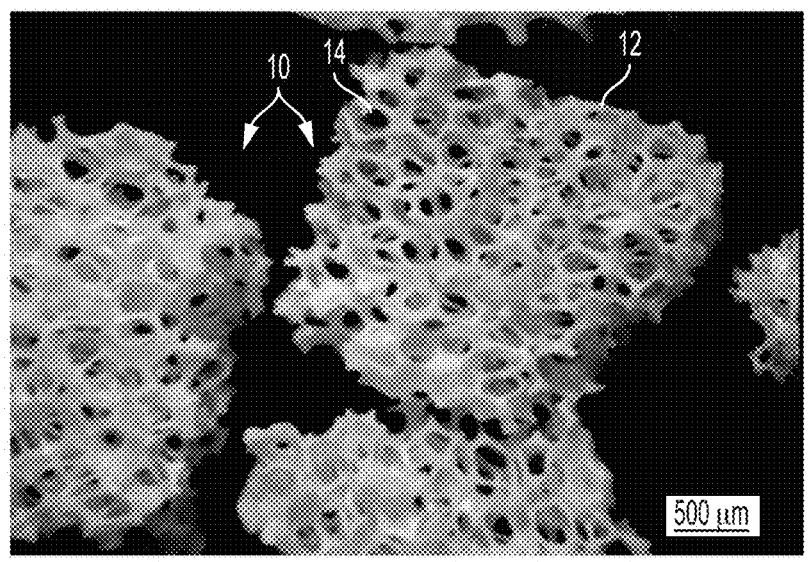
FIG. 1 is a scanning electron microscope (SEM) image of porous hydroxyapatite granules.

The extracellular matrix of hard tissues is composed of two distinct phases, an organic phase and an inorganic phase. The inorganic portion of bone is comprised mainly of hydroxyapatite while the organic phase is primarily comprised of type I collagen and smaller amounts of other proteins. Structurally, although hard, bone is a porous material, with porosities of 50-90% in trabecular bone and 3-12% in cortical bone. By providing a substrate containing osteogenic progenitor cells, in combination with the biological binding cues from the organic phase as well as some of the mechanical rigidity seen in the inorganic phase, it may be possible to produce a fully functional device capable of supporting osteogenic differentiation as well as new bone growth. In certain embodiments, the organic phase contains growth factors and/or proteins that aid in the repair process.

Calcium phosphate based materials are a popular synthetic bone graft material because they have been shown to demonstrate an ability to incorporate within natural bone, as well as have osteoconductive properties. Two of the most widely researched materials of this type are hydroxyapatite and β-tricalcium phosphate (β-TCP). Hydroxyapatite has high biocompatibility, good bioaffinity, has been shown to stimulate osteoconduction, and can be further integrated/replaced by the host bone after implantation. Porosity of hydroxyapatite has been shown to be incredibly important in osteogenic differentiation on both a micro and macro level of organization. In combination with rigid plating to provide mechanical support, hydroxyapatite materials have demonstrated an ability to fully incorporate and patients reported significant decreases in pain. One limitation in this type of therapy is that the scaffold must have a high surface area and a high degree of surface contact with the bone for the implantation to be successful. Moldable formulations may be preferred as compared to rigid scaffolds in that they can take the shape of any treatment space. By the using moldable substrates, a surgeon would not need to fit the surgical site around the implant or modify the implant to fit the target space. Ultimately, this will reduce surgical time, as well as avoid additional bone loss or trauma to the surrounding tissue area.

Because cells need specific substrates to drive differentiation, particle formulations combined with a delivery vehicle have been investigated. By utilizing a microparticle based system, it is possible to capitalize on the osteogenic properties of the scaffold material, but use it in a moldable formulation. Additionally, particulate based formulations have a much higher surface area, which may alter the degradation rates of the materials resulting in faster implant incorporation. By includingg a matrix system to hold the microparticles together, it is possible to add not only better handling properties, but also increase cell affinity/bioactivity of the inventive implant. Further, the particles can be used to incorporate an extra dimension of porosity in that the spaces between tightly packed particles can be used to create interconnected pores throughout the implant.

Collagen (type I) is the most abundant extracellular protein of bone, the structure of which has been shown to be important for cell attachment, proliferation and differentiation. Gelatin, a derivative of collagen, is biocompatible and biodegradable and has been widely investigated as a carrier material for other biological agents in bone applications. Further, incorporation of gelatin has been shown to increase cell adhesion as well as proliferation of cells. This effect has been demonstrated in a variety of ways, most notably in simple coating procedures. When combined with hydroxyapatite particles, particles incorporating gelatin showed significantly enhanced cell binding as compared to hydroxyapatite particles alone. Other naturally derived biopolymers have been investigated as scaffold-based materials including alginate, chitosan, and fibrin.

With inclusion of autologous, patient-derived factors, including cells and proteins, the full therapeutic potential of this type of device can be realized. While hydrating implantable materials with bone marrow aspirate has been investigated, the effects of cell concentration often are not considered. In critical-sized, long bone non-unions, a greater than physiological concentration of progenitor cells was shown to promote bony union. Incorporating autologous growth factors and proteins within the matrix material will provide additional support to amplify the beneficial effects of the cells. Growth factors can act to aid in tissue repair in a number of ways. One of the essential steps in wound repair is the generation of new blood vessels in order to ensure the delivery of nutrients, as well as facilitate removal of waste products and debris. Vascular endothelial growth factor ("VEGF"), for example, is a potent angiogenic factor that is capable of stimulating endothelial cell migration and activation, as well as angiogenesis. Further, VEGF has been shown to have a significant role in bone repair. Plate-derived growth factor ("PDGF"), another growth factor found in plasma, is a potent mitogenic and chemotactic factor for a variety of cells, including fibroblasts and smooth muscle cells. The presence of growth factors and cytokines within the matrix will encourage recruitment of additional host cells within the defect and help to further reduce the time necessary for tissue formation and repair of the pathology.

The inventive process and methods are an improvement on the art of using a bone void filler in that it combines all necessary factors in the healing cascade in a concentrated manner, maximizing the regenerative capabilities of the implanted device. The scaffold material offers the ability to not only offer a substrate that the concentrated cells will preferentially bind to, but also be adsorbed as new tissue is formed, allowing for complete repair of tissue. The addition of autologous growth factors will recruit other necessary cells from the surrounding host tissue, thus further augmenting the healing cascade.

DESCRIPTION OF EXEMPLARY EMBODIMENTS

A cellular component is defined as a fluid containing cells, some of which are known to be progenitors of bone-forming cells that are capable of making extracellular matrix resembling native bone tissue, with a composition that is not naturally occurring in the body. Examples of the inventive device include the following:
  a. Autologous bone marrow concentrated and/or filtered to remove red blood cells, while retaining growth factors and mononuclear cells at a concentration greater than 1.1 X.
  b. Autologous bone marrow concentrated and/or filtered to remove all other extracellular components at a concentration greater than 1.1 X.
  c. Autologous adipose tissue filtered, enzymatically digested, and/or concentrated to isolate known progenitor cells at a concentration greater than 1.1 X natural cell concentration.
  d. Autologous progenitor cells that have been isolated and expanded ex vivo to be 1.1 X or more the concentration of the cells found in native tissue.
  e. Allogeneic progenitor cells that are 1.1 X or more the concentration of the cells found in native tissue.
  f. Any combination of the above.

The inorganic matrix part of the scaffold material is defined as a porous particle such that it mimics the inorganic portion of natural bony tissue. Examples include the following:
  a. The inventive matrix can be formulated in a variety of formats, including a granule form, a powder form, a strip formand a block form.
  b. Porosity will mimic that found in bone ranging from 50-95% or 3-15% porosity.
  c. Granule composition may include calcium phosphate, mono calcium phosphate, tricalcium phosphate, tetra calcium phosphate, octacalcium phosphate, hydroxyapatite, carbonate apatite, fluoro apatite, or any combination thereof.
  d. The granule composition may also contain materials to mimic the ionic characteristics of bone, this may include (but is not limited to): silicon, strontium, or magnesium.

The organic matrix part of the scaffold material is defined as an organic biopolymer either natural or synthetic that would act to aid in cell retention as well as render the scaffold in a moldable format. The organic matrix can be made up of a single biopolymer or a mixture of biopolymers. Examples include the following:
  a. The biopolymer may be selected from one of the following: collagen, gelatin, fibrinogen, vitronectin, fibronectin, albumin, peptides, chitin, alginate, cellulose, carboxymethycellulose or any combination thereof Growth factors and cytokines are proteins that can be found autologously in blood and bone marrow but delivered in a concentrated form not found naturally within the body. Examples include the following:
  a. The growth factors and cytokines can be autologous and concentrated from biological fluids including the platelet poor fraction of blood or bone marrow
  b. The growth factors and cytokines can be synthetically derived and incorporated within the scaffold at the discretion of the physician A clotting agent may be added at the discretion of the physician to the device in order to preferentially alter the handling characteristics of the implant.

Animal Study

A total of 33 New Zealand White rabbits were evaluated with both the test and control articles in an animal study. For each rabbit, after anesthetization, bone marrow was harvested from the iliac crest and both the test and predicate device was hydrated (separately) with autologous bone marrow prior to implantation. Samples of the aspirate were retained for further in vitro regenerative analysis. Two drill defects were created in each rabbit (approximately 5-6 mm in diameter and 8-10 mm in length). Once the test and control sites were prepared, the test articles and control articles were implanted into the femoral condyles, each on a separate side. The surgical sites were closed, and the animals were observed daily for 4, 8, and 13 weeks. At 4, 8, and 13 week time points, 10 rabbits were euthanized (at the 13 week time point, all remaining rabbits are euthanized). The test article and control article implant sites as well as the draining lymph nodes were explanted at necropsy. All tissues were fixed in an appropriate fixative.

Characterization and Comparison of HA Components

FIG. 1 is an SEM image of porous hydroxyapatite granules. A granule 10 is shown comprising a scaffold 12. In comparison to other commercially available granules, the scaffold 12 forms a plurality of voids 14 throughout the granule 10. The plurality of voids 14 increases a surface area of the granule 10, which increase facilitates one or more of faster implant incorporation, better handling properties, increased cell affinity/bioactivity, and an overall increase in porosity of in an area of application.

Figure 2:
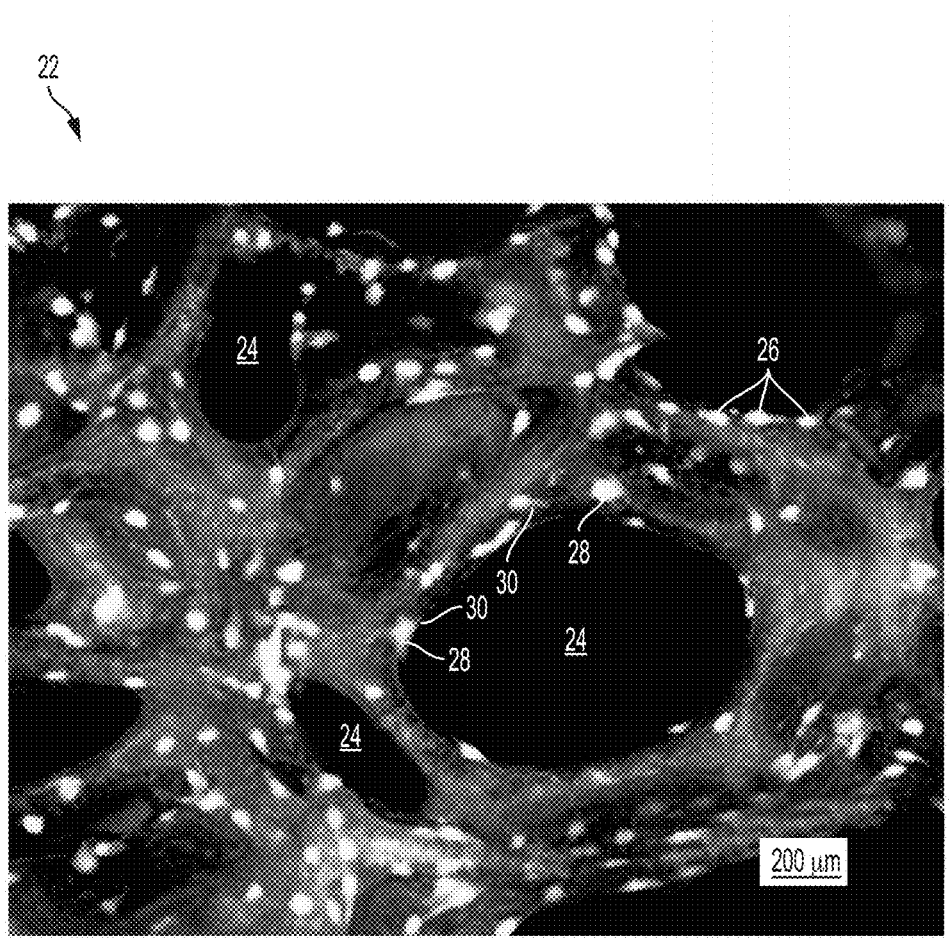
FIG. 2 is an enhanced image showing mesenchymal stem cells proliferated on a porous hydroxyapatite scaffold in vitro.

FIG. 2 is an enhanced image showing mesenchymal stem cells 26 proliferated on a porous hydroxyapatite scaffold 20 in vitro. The porous hydroxyapatite scaffold 20 comprises a structure of a granule 22. The granule 22 may be similar to the granule 10 showin in FIG. 1. The porous hydroxyapatite scaffold 20 comprises a plurality of voids 24, which plurality of voids 24 increases a surface area of the granule 22. Each of the plurality of mesenchymal stem cells 26 comprises a nucleus 28 and fibrillar actin 30. The nuclei 28 are shown in FIG. 2 as white spots disposed on the porous hydroxyapatite scaffold 20. The fibrillar actin 28 is indicated in FIG. 2 by light gray areas surrounding the nuclei 26. The increased surface area provided to the granule 22 by the plurality of voids 24 results in an increased proliferation of mesenchymal stem cells 26 compared to other non-void-containing granules.

Histopathological Analysis

Each implant section was analyzed by a pathologist for local tissue reaction following ISO 10993-6 guidelines, as well as any osteoconductivity, bone growth, and/or bone development within the defect. The test article was compared to the control article. The histopathology data was used to evaluate both local tissue reactions as well as bone formation.

Figure 3:
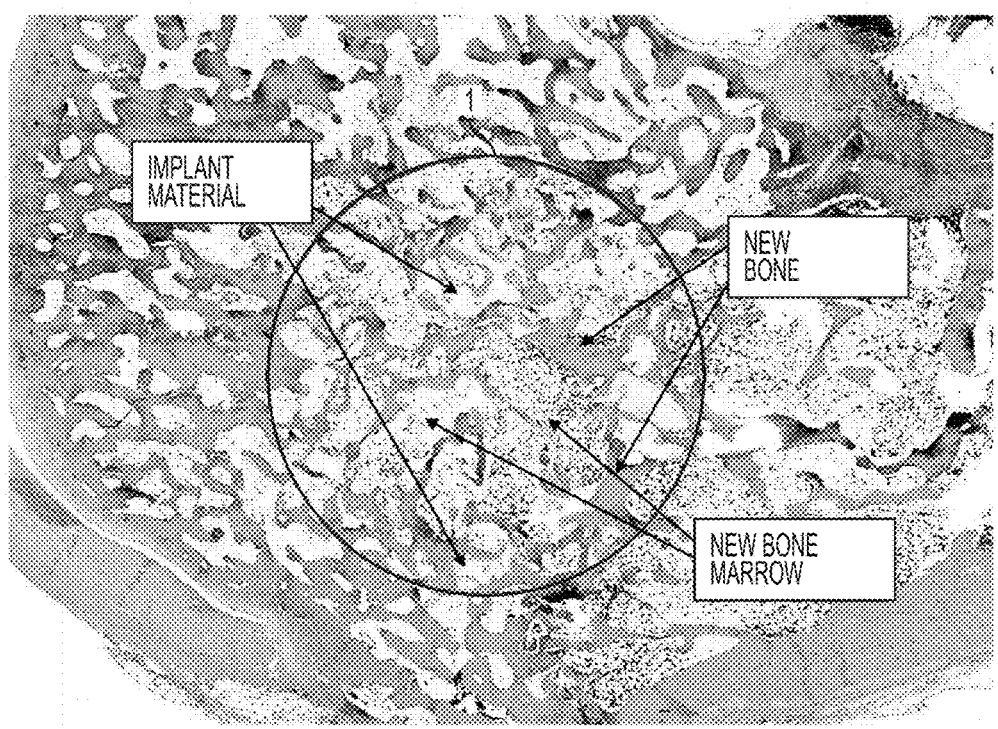
FIG. 3 is an image of a thirteen week test article implant site.
Figure 4:
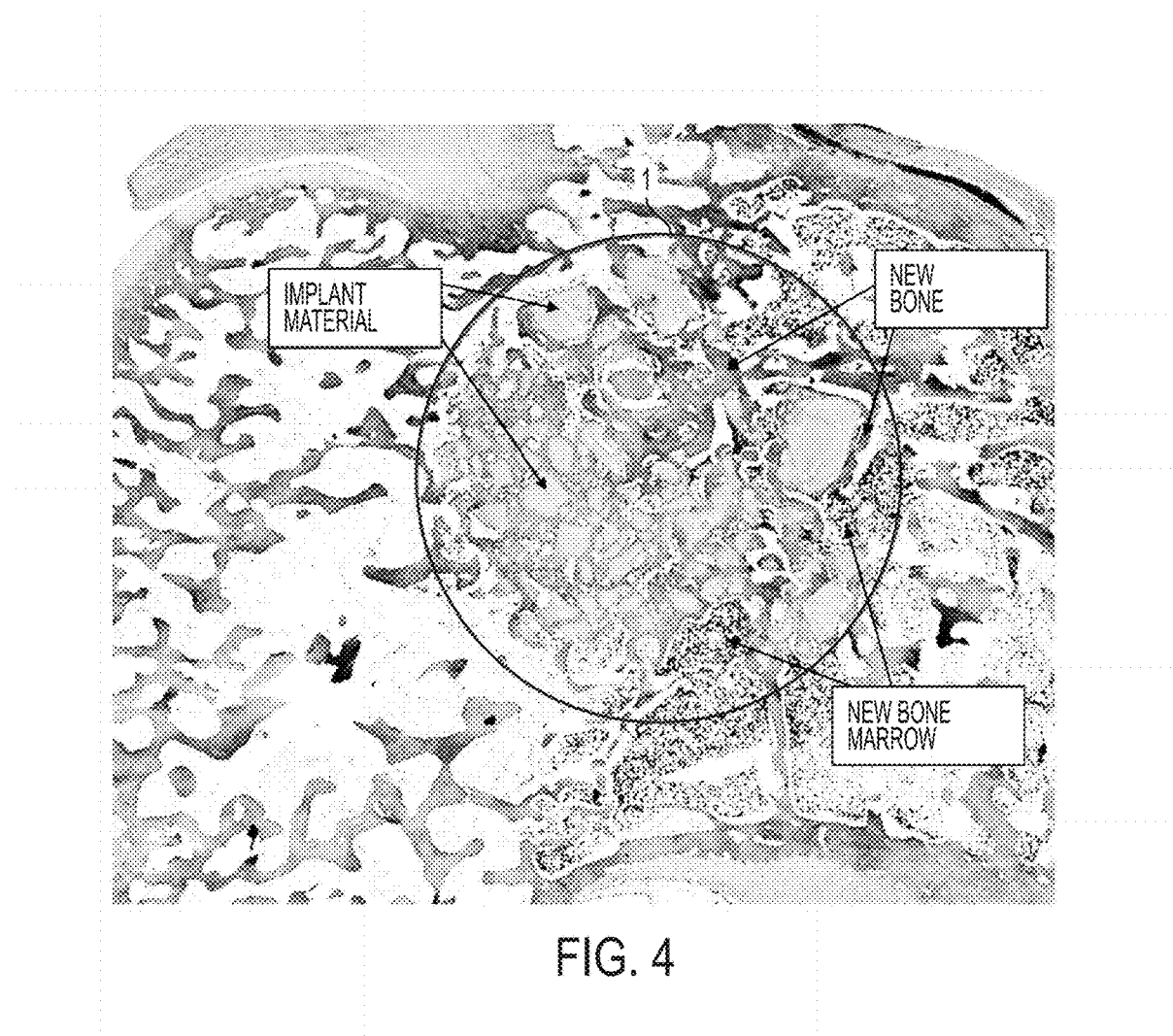
FIG. 4 is an image of a thirteen week control article implant site.

FIGS. 3 and 4 demonstrate histology results for a test article and a control article after a 13 week period, respectively. FIG. 3 shows that implanting porous hydroxyapatite granules was as effective as the predicate control article at promoting new bone development in a defect by having similar tissue responses surrounding the implant sites and within the implant sites as the control article at all durations. Implanting porous hydroxyapatite granules also had faster resorption and increased new bone formation within the implant sites compared to the control article.

High-Resolution MicroCT Bone Imaging

Rabbit condyles were scanned using micro-computer tomography (MicroCT) to visualize new bone formation. The specimens were processed to obtain 3D images in addition to quantitative measurements of bone and material volumes, densities, and trabecular features. All samples were scanned on a high-resolution, volumetric microCT scanner.

Using a documented segmentation process, regions of interest were defined using VHLab software and values were assigned to each voxel in order to be used later for quantitative analysis. Voxel counts were then used to determine the following volume measurements: bone volume (BV), material volume, and total volume (TV) (this would be the total volume of the region of interest). Trabecular morphometric analysis was also performed within the region of interest to determine connectivity density, structure model index, trabecular number, trabecular thickness, trabecular spacing, bone surface, bone surface per bone volume (BS/BV) and mean bone density.

MicroCT analysis of samples where autologous bone marrow aspirate with porous hydroxyapatite granules revealed that the porous hydroxyapatite granules proved to be more effective than implanting autologous bone marrow aspirate with non-porous granules with regard to spurring new bone growth, while also degrading/resorbing more quickly than a control material. New bone formed in samples implanted with porous hydroxyapatite granules had higher mineral density and was less porous and structurally more similar to mature bone. Differences between test and control samples were larger at 13-weeks than 8-weeks for every parameter other than trabecular number and spacing and material volume.

In the preceding detailed description, the invention is described with reference to specific exemplary embodiments thereof. Various modifications and changes may be made thereto without departing from the broader spirit and scope of the invention as set forth in the claims. The specification and drawings are, accordingly, to be regarded in an illustrative rather than a restrictive sense.

The invention claimed is:

1. A filler combining both autologous and synthetic materials for repair or regeneration of bone tissue, said filler comprising:
   a synthetic scaffold matrix comprised of at least one porous granule, the at least one porous granule having a porosity of between either about 50% and about 95% by volume or between about 3% and about 15% by volume, wherein each porous granule of the at least one porous granule is formed from a composition selected from the group consisting of: mono calcium phosphate, tetra calcium phosphate, octacalcium phosphate, carbonate apatite, fluoro apatite;
   an autologous cellular component; and
   an organic biopolymer, the organic biopolymer comprising at least one of gelatin, alginate, and chitosan.

2. The filler of claim 1, further comprising a growth factor.

3. The filler of claim 2, wherein the growth factor comprises at least one of vascular endothelial growth factor and platelet-derived growth factor.

4. The filler of claim 2, wherein the growth factor is an autologous growth factor that has been concentrated from a biological fluid.

5. The filler of claim 4, wherein the biological fluid comprises at least one of a platelet poor fraction of blood and bone marrow.

6. The filler of claim 2, further comprising a synthetically derived cytokine.

7. The filler of claim 2, wherein the growth factor is a synthetically derived growth factor.

8. The filler of claim 1, wherein the autologous cellular component comprises autologous bone marrow.

9. The filler of claim 8, wherein the autologous bone marrow is filtered to remove at least one of red blood cells and extracellular components.

10. The filler of claim 1, wherein the autologous cellular component comprises autologous adipose tissue.

11. The filler of claim 10, wherein the autologous adipose tissue comprises progenitor cells.

12. The filler of claim 1, wherein the autologous cellular component comprises concentrated autologous progenitor cells.

13. The filler of claim 1, further comprising a clotting agent.

14. The filler of claim 1, wherein each porous granule of the at least one porous granule further comprises one or more of silicon and strontium.

15. A filler combining both autologous and synthetic materials for repair or regeneration of bone tissue, said filler comprising:
   a synthetic scaffold matrix comprised of at least one porous granule, the at least one porous granule having a porosity of between either about 3% and about 15% by volume or between about 50% and about 90% by volume, wherein each porous granule of the at least one porous granule comprises one or more of silicon or strontium;
   an autologous cellular component; and
   an organic biopolymer, the organic biopolymer comprising at least one of gelatin, alginate, and chitosan.

* * * * *